US011660076B2

(12) United States Patent
Kajiyama et al.

(10) Patent No.: US 11,660,076 B2
(45) Date of Patent: May 30, 2023

(54) ULTRASONIC PROBE, ULTRASONIC DIAGNOSTIC APPARATUS, AND ULTRASONIC TRANSMISSION/RECEPTION SWITCHING METHOD

(71) Applicant: Hitachi, Ltd., Tokyo (JP)

(72) Inventors: Shinya Kajiyama, Tokyo (JP); Kengo Imagawa, Tokyo (JP); Yoshihiro Hayashi, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 369 days.

(21) Appl. No.: 16/596,917

(22) Filed: Oct. 9, 2019

(65) Prior Publication Data

US 2020/0163652 A1 May 28, 2020

(30) Foreign Application Priority Data

Nov. 27, 2018 (JP) .............................. JP2018-221349

(51) Int. Cl.
*A61B 8/00* (2006.01)
*G01S 7/52* (2006.01)

(52) U.S. Cl.
CPC ................. *A61B 8/54* (2013.01); *A61B 8/44* (2013.01); *G01S 7/52077* (2013.01)

(58) Field of Classification Search
CPC ........... A61B 8/54; A61B 8/56; A61B 8/5207; A61B 8/44; G01S 7/52077; G01S 7/52079; G01S 15/8927
See application file for complete search history.

(56) References Cited

U.S. PATENT DOCUMENTS

| 4,704,642 A * | 11/1987 | Namiki ................... G11B 20/24 |
| 5,269,189 A * | 12/1993 | Thompson .............. G01N 29/22 73/632 |
| 2012/0249210 A1 | 10/2012 | Shimizu et al. |
| 2016/0183927 A1* | 6/2016 | Kremsl ................ A61B 8/5269 600/443 |
| 2016/0380640 A1* | 12/2016 | Boser .................. G01S 7/52004 367/13 |
| 2017/0188996 A1* | 7/2017 | Kajiyama ............. A61B 8/4483 |

(Continued)

FOREIGN PATENT DOCUMENTS

| JP | 59-222139 A | 12/1984 |
| JP | 2006-325044 A | 11/2006 |
| JP | 2012-209763 A | 10/2012 |

(Continued)

OTHER PUBLICATIONS

Japanese-language Office Action issued in Japanese Application No. 2018-221349 dated Jun. 14, 2022 with English translation (six (6) pages).

*Primary Examiner* — Christopher Koharski
*Assistant Examiner* — Taylor Deutsch
(74) *Attorney, Agent, or Firm* — Crowell & Moring LLP

(57) ABSTRACT

A switch circuit connected to a transducer, a reception circuit connected to the switch circuit, a first switch element connected to a reception terminal provided between the switch circuit and the reception circuit, a first resistance element connected to a control terminal of the switch circuit, a second resistance element provided inside the reception circuit, and a second switch element provided inside the reception circuit are provided.

12 Claims, 11 Drawing Sheets

(56) References Cited

U.S. PATENT DOCUMENTS

2017/0252001 A1   9/2017   Shibanuma et al.
2018/0035974 A1   2/2018   Kajiyama et al.

FOREIGN PATENT DOCUMENTS

| JP | 2017-153750 A | 9/2017 |
| WO | WO 2015/189982 A1 | 12/2015 |
| WO | WO 2016/152375 A1 | 9/2016 |

* cited by examiner

ULTRASONIC PROBE, ULTRASONIC DIAGNOSTIC APPARATUS, AND ULTRASONIC TRANSMISSION/RECEPTION SWITCHING METHOD

BACKGROUND OF THE INVENTION

1. Field of the Invention

The present invention relates to an ultrasonic probe, an ultrasonic diagnostic apparatus, and an ultrasonic transmission/reception switching method.

2. Description of the Related Art

The ultrasonic diagnostic apparatus is a medical diagnostic apparatus that is non-invasive and highly safe to the human body, and the scale of the apparatus is smaller than other medical image diagnostic apparatuses such as an X-ray diagnostic apparatus and an MRI (Magnetic Resonance Imaging) apparatus. In addition, because it is an apparatus that can display in real time the movement of the test object, such as heart pulsation and movement of the fetus, by a simple operation that only applies the ultrasonic probe from the body surface, ultrasonic diagnostic apparatuses play an important role in today's medical care.

In the ultrasonic diagnostic apparatus, ultrasonic waves are transmitted into the subject by supplying a high voltage drive signal to each of a plurality of transducers incorporated in the ultrasonic probe. Reflected waves of ultrasonic waves generated due to the difference in acoustic impedance of the living tissue in the subject are respectively received by a plurality of transducers, and an image is generated based on the reflected waves received by the ultrasonic probe.

Specifically, in transmission, acoustic pulses are focused by driving the transducers by giving independent delays to a plurality of transducers, and ultrasonic beam forming and beam scanning are performed. In reception, in order to compensate for the difference in the distance from the reflection point in the living body to each transducer, phasing processing is performed which gives an independent delay to a plurality of transducers to coherently align the phases of the signals, and adds these. As described above, ultrasonic imaging requires a transmission operation and a reception operation, and inevitably involves switching from transmission to reception. At this time, a virtual image is generated due to electrical noise caused by switching from transmission to reception, and transmission/reception switching noise is input to the reception system to cause a problem of signal loss due to saturation of the reception circuit.

In recent years, ultrasonic diagnostic apparatuses capable of obtaining a three-dimensional stereoscopic image have been developed, and inspection efficiency can be improved by specifying an arbitrary cross section from the three-dimensional stereoscopic image to obtain a tomogram. For three-dimensional imaging, it is necessary to change the transducers in the ultrasonic probe from the conventional one-dimensional array to the two-dimensional array, that is, a 2D array, and the number of transducers increases with the square of the number of transducers in the conventional ultrasonic probe. In this case, it is impossible to increase the number of cables connecting the ultrasonic probe and the main unit by a square. For this reason, it is necessary to transfer received signals whose number is reduced by phasing addition in the ultrasonic probe to the main unit via a cable.

In order to realize such phasing addition in the ultrasonic probe, the functions of transmission and reception and phasing addition are realized as a beam former IC, and a transmission/reception circuit is disposed for each transducer in the IC and will be electrically connected to the transducer in a one-to-one manner. The arrangement pitch of the transducers is determined by the condition of diffraction, and is determined by the frequency of the ultrasonic wave and the scanning angle of the ultrasonic beam so that grating lobes which are generated by diffraction separately from the main lobe appear out of the scanning angle of the ultrasonic beam. That is, the area of the transmission/reception circuit for each transducer in the IC is restricted by the arrangement pitch of the transducers, and a transmission/reception circuit having a small area is required.

The transmission/reception switching noise is generated mainly due to transition from the OFF state to the ON state of a TRSW (Transmit/Receive-Switch, transmission/reception separation switch) disposed between the high voltage transmission circuit and the low voltage reception circuit to protect the reception circuit from the transmission high voltage signal. When taking measures against the transmission/reception switching noise with a circuit, it is necessary to take measures with a small-scale and simple circuit because of the circuit area restriction as described above.

JP 2012-209763 A describes that such transmission/reception switching-induced noise is reduced.

SUMMARY OF THE INVENTION

JP 2012-209763 A prevents the switching current flowing to the latch from flowing to the source side of the transmission/reception separation switch and becoming noise.

However, with JP 2012-209763 A, it is difficult to effectively reduce transmission/reception switching noise that is generated along with ultrasonic transmission/reception switching.

An object of the present invention is to effectively reduce transmission/reception switching noise generated along with ultrasonic transmission/reception switching in an ultrasonic diagnostic apparatus.

The ultrasonic probe according to one aspect of the present invention includes a transducer, a switch circuit connected to the transducer, a reception circuit connected to the switch circuit, a first switch element connected to a reception terminal provided between the switch circuit and the reception circuit, a first resistance element connected to a control terminal of the switch circuit, a second resistance element provided inside the reception circuit, and a second switch element provided inside the reception circuit.

The ultrasonic diagnostic apparatus according to one aspect of the present invention includes: an ultrasonic probe including a plurality of transducers, a transmission/reception circuit that is provided corresponding to each of the plurality of transducers and switches an ultrasonic wave from transmission to reception, an adder circuit that adds outputs of a plurality of the transmission/reception circuits, and a control circuit that controls the transmission/reception switching; and a main unit that receives the output of the adder circuit and transmits a predetermined control signal to the control circuit, the ultrasonic probe having a switch circuit connected to the transducer, a reception circuit connected to the switch circuit, a first switch element connected to a reception terminal provided between the switch circuit and the reception circuit, a first resistance element connected to a control terminal of the switch circuit, a second resistance element provided inside the reception circuit, and a second switch element provided inside the reception circuit.

The ultrasonic transmission/reception switching method according to one aspect of the present invention includes switching from transmission to reception without performing ultrasonic transmission before imaging a frame or volume composed of a plurality of scanning lines, acquiring first received beam data corresponding to transmission/reception switching noise generated upon switching from the transmission to the reception, thereafter performing normal ultrasonic transmission and reception to acquire second received beam data, and subtracting the first received beam data from the second received beam data.

According to one aspect of the present invention, it is possible to effectively reduce transmission/reception switching noise generated along with ultrasonic transmission/reception switching in the ultrasonic diagnostic apparatus.

DESCRIPTION OF THE PREFERRED EMBODIMENTS

First, the related art will be described with reference to FIG. 11.

Figure 11:
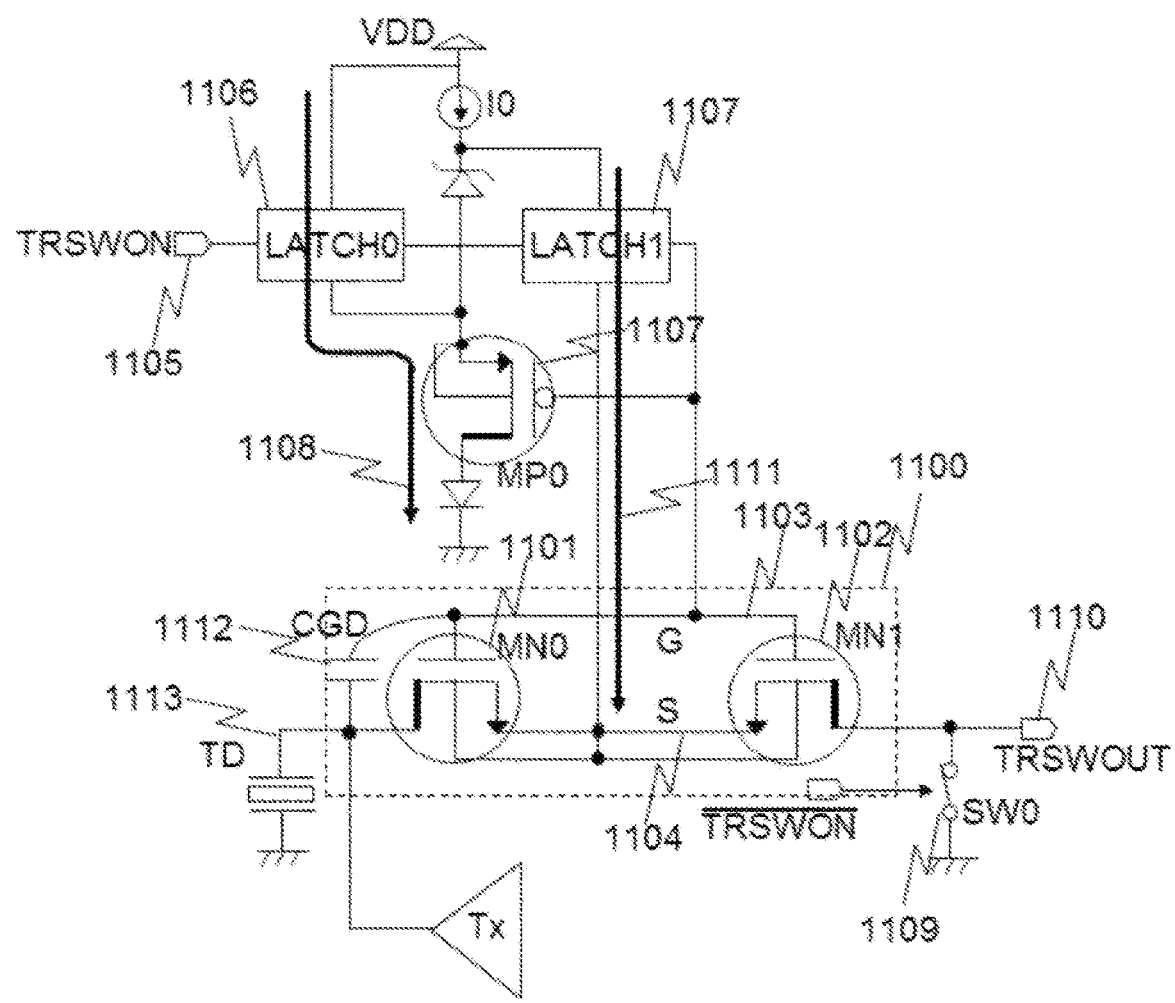
FIG. 11 is a diagram showing a circuit configuration of the related art.

As shown in FIG. 11, a TRSW 1100 has a configuration in which a gate 1103 and a source 1104 of two MOSFETs MN0 1101 and MN1 1102 are connected to each other. The on/off state is obtained by applying a predetermined positive voltage to a voltage VGS between a gate G and a source S or by setting the voltage to 0V. In order to generate a predetermined VGS or 0V, the voltage between the gate 1103 and the source 1104 is controlled by level-shifting the reception/transmission, that is, an on/off control signal TRSWON 1105 by two latches LATCH0 1106 and LATCH1 1107.

When a through current 1108 flows to the source 1104 when the latch is inverted, noise is generated and is input from a TRSWOUT 1110 to the reception circuit. Therefore, a circuit configuration is adopted in which the through current 1108 during switching of the LATCH0 1106 flows to GND through an MP0 1107 so that it does not flow to the source 1104, and thus transmission/reception switching noise is reduced. Further, by providing an SW0 1109 and turning on the SW0 1109 during the transmission period, the noise input from the TRSWOUT 1110 to a reception system at the time of transmission is reduced to improve the isolation of transmission and reception.

However, in FIG. 11, although it can be avoided that the through current 1108 during switching of the LATCH0 1106 contributes to noise, a through current 1111 during switching of the LATCH 1 flows to the source 1104 and becomes noise. In addition, when the VGS increases from 0V to a predetermined voltage, generation of spike noise in a transducer (TD) 1113 due to capacitive coupling via a CGD 1112 which is a gate-drain parasitic capacitance of the MN0 1101 cannot be avoided.

Furthermore, although the SW0 1109 contributes to the improvement of transmission/reception isolation, it does not contribute to the reduction of transmission/reception switching noise since the SW0 1109 is turned OFF simultaneously with transition to reception.

From such a point, there is a need for a method of effectively reducing transmission/reception switching noise generated along with ultrasonic transmission/reception switching. In particular, there is a need for a method of reducing noise due to parasitic capacitance CGD coupling of a MOSFET which is essentially generated by TRSW in which two MOS transistors (MOSFETs) are connected in series.

Furthermore, there is a need for a method of reducing the influence of the saturation of the reception circuit, which is a problem when the noise is input to the reception circuit, and the influence of the saturation of the rear-stage circuit due to the saturation of the preamplifier, and of shortening a reception impossible period by recovering from the saturation in a short time.

The embodiment reduces a virtual image caused by transmission/reception switching noise generated upon switching from transmission to reception of ultrasonic waves. In addition, it is possible to shorten the reception impossible period due to the saturation of the reception circuit caused by the input of the transmission/reception switching noise to the reception circuit and to receive echo from near the body surface.

Also, the embodiment reduces the transmission/reception switching noise by limiting the gate charging current of the transmission/reception separation switch or fixing the reception input to GND. Furthermore, by raising the time constant of the high pass characteristic of the reception circuit and stopping the output of the reception circuit, the recovery from the circuit saturation accompanying the input of the switching noise to the reception circuit is accelerated to prevent the saturation of the rear-stage circuit. Thus, the state is sequentially switched from the state different from the steady reception state to the steady reception state. As a result, the virtual image due to the transmission/reception switching noise is reduced, and the reception impossible period in which an image cannot be obtained is shortened.

Hereinafter, embodiments will be described using the drawings.

First Embodiment

The circuit configuration of the ultrasonic probe of the first embodiment will be described with reference to FIGS. 1 and 2.

At the time of ultrasonic transmission, a transmission circuit (Tx) 110 drives a transducer (TD) 100 with a high voltage pulse, the transducer 100 performs electrical/mechanical conversion, and an acoustic pulse is transmitted into the living body. At the time of transmission, a switch circuit (TRSW) 101 composed of two MOSFETs is turned off to prevent a low-voltage reception low noise amplifier (LNA) 111 from being destroyed by the high voltage pulse output from the transmission circuit 110. The switch circuit (TRSW) 101 can be turned off by setting the voltage between the gate (G) 114 and the source (S) 115 to 0V by turning off the switch (SW0) 112 and turning on the switch (SW1) 113.

To switch from transmission to reception, a control signal (TRSWON) is made to transition from Lo level to Hi level. As a result, the switch 112 is turned on, the switch 113 is turned off, and the voltage VGS between the gate (G) 114 and the source (S) 115 increases. At this time, since VGVDD is Lo as shown in FIG. 2, the switch (SW2) 116 is in the OFF state, and a current flows from VDD to the gate (G) 114 through a resistor (R0) 117. The charging current is limited by the resistor 117, and VGS rises slowly, whereby transmission/reception switching noise superimposed on the transducer 100 can be reduced.

At this time, a GSHT 118 is Hi, and the transmission/reception switching noise superimposed on the transducer 100 passes through the switch circuit 101. However, a switch (SW3) is turned on to suppress transmission/reception switching noise with low impedance, and the transmission/reception switching noise input to the reception low noise amplifier 111 side can be reduced.

The transducer 100 operates around 0V during transmission and reception, at the time of transmission, for example, in case of three-value pulse transmission, transmits a pulse composed of three values, that is, a positive high voltage, a negative high voltage, and a 0V, and also at the time of reception, receives a signal with 0V as a common potential. Here, in order to receive 0V common, the reception circuit 103 needs a positive voltage and a negative voltage, and the type of power supply increases.

In order to prevent this, a capacitor (C0) 119 may be inserted in series in the reception signal path to be AC coupled. That is, by forming a high-pass filter including the capacitor 119 and a resistor (R1) 120, the DC potential on the reception low noise amplifier 111 side of the capacitor 119 can be determined again. Therefore, by setting an appropriate positive voltage to a common potential (VCM) 121, the reception circuit 103 after the reception low noise amplifier 111 can be operated between the positive VDD and GND, and the negative power supply becomes unnecessary.

Here, immediately after the reception transition, a switch (SW4) 123 is on because an LNAMUTE 122 is Hi. As a result, the low frequency side of the normal reception passband is determined by the capacitor 119 and the resistor 120, but immediately after the reception transition it is determined by the capacitor 119 and the on resistance of the switch 123.

That is, the cutoff frequency of the high pass filter immediately after the reception transition is higher than that of the normal reception state. Temporarily, when large amplitude transmission/reception switching noise passes through the capacitor 119, the time when the input of the reception low noise amplifier 111 returns to the original common potential 121 from here is determined not by a large time constant determined from the capacitor 119 and the resistor 120 but by a small time constant determined by the capacitor 119 and the on resistance of the switch 123. Therefore, even if transmission/reception switching noise passes through the capacitor 119, by turning on the switch 123, it is possible to shorten the time until the input of the reception low noise amplifier 111 returns to the VCM 121, and return from circuit saturation can be performed in a short time.

Further, immediately after the reception transition, the LNAMUTE signal 122 is set to Hi to turn on a switch (SW5), and the reception low noise amplifier 111 is set to a state in which the differential signal does not appear at the output (OUTP-OUTN) 109 thereof and the gain is substantially close to zero. Thus, even when transmission/reception switching noise is input to the reception low noise amplifier 111, it is possible to prevent saturation of the rear stage without transmitting the transmission/reception switching noise to the rear stage.

Organize the above. As shown in the timing chart of FIG. 2, immediately after TRSWON transitions from Lo to Hi, the transmission/reception switching noise superimposed on the transducer 100 is reduced by slow rising of the VGS of the switch circuit 101. Also, by suppressing the output of the switch circuit 101 to GND by the switch SW3, noise input to the reception low noise amplifier 111 is suppressed, and in the state where the switch 123 is turned on, the high pass filter is in a state of being able to recover in a short time also from the circuit saturation due to transmission/reception switching noise, and the reception low noise amplifier 111 is in a state of stopping the output and not saturating the rear stage.

From this state, although not particularly limited, the state of each circuit is made to transition from the side close to the transducer 100 toward the rear stage so as to be in the original reception state. VGVDD is raised to Hi, and the gate 114 of the switch circuit 101 is brought to the original impedance in the steady reception state. Also at this time, noise is generated, but the noise input to the reception low noise amplifier 111 can be suppressed because the GSHT is Hi. Noise is also generated when GSHT is lowered to allow a signal to be input to the reception low noise amplifier 111. However, even if saturation occurs due to this noise, since the LNAMUTE is Hi and the cutoff frequency of the high pass filter is high, it is possible to recover from the saturation in a short time. Finally, the LNAMUTE is lowered to Lo so as to allow even the low band signal to pass through the high pass filter, so that the reception low noise amplifier 111 can output the signal to the rear stage.

As understood from the above, noise is also generated when the state of the circuit is made to transition to the steady reception state. Therefore, instead of taking measures by taking two states with a single circuit, the states of a plurality of circuits are set to noise suppressible states, and these are sequentially canceled and made to transition to a steady reception state, and thus making it possible to effectively suppress noise or to recover in a short time from saturation due to noise or to prevent propagation to the rear stage.

Figure 2:
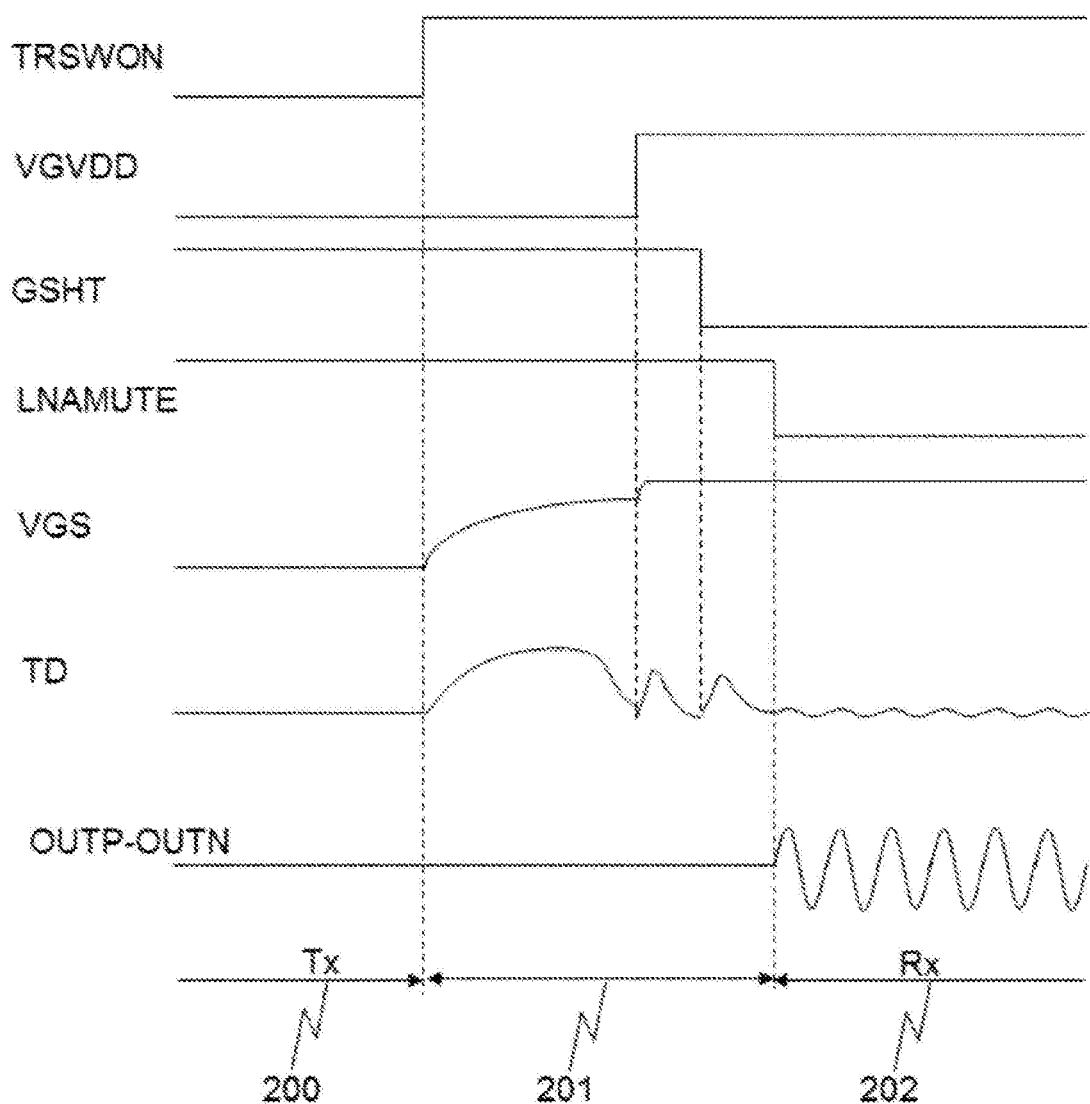
FIG. 2 is a timing chart illustrating the operation of the ultrasonic probe of the first embodiment.

The sequence shown in FIG. 2 is not particularly limited, and some measures in each circuit may be omitted depending on the absolute value of the generated noise, or the order of state transition may be interchanged.

According to the sequence of FIG. 2, there is a period in which the original reception cannot be performed between the state of transmission (Tx) 200 and the state of reception (Rx) 202. For this reason, after transmitting an ultrasonic wave, it will not be able to receive an echo reflected and returned at the immediate vicinity of the body surface. Therefore, it is necessary to set the reception impossible period equal to or less than the ultrasonic round trip time to the shallowest point in the vicinity of the body surface where the ultrasonic image is desired to be acquired.

Figure 3:
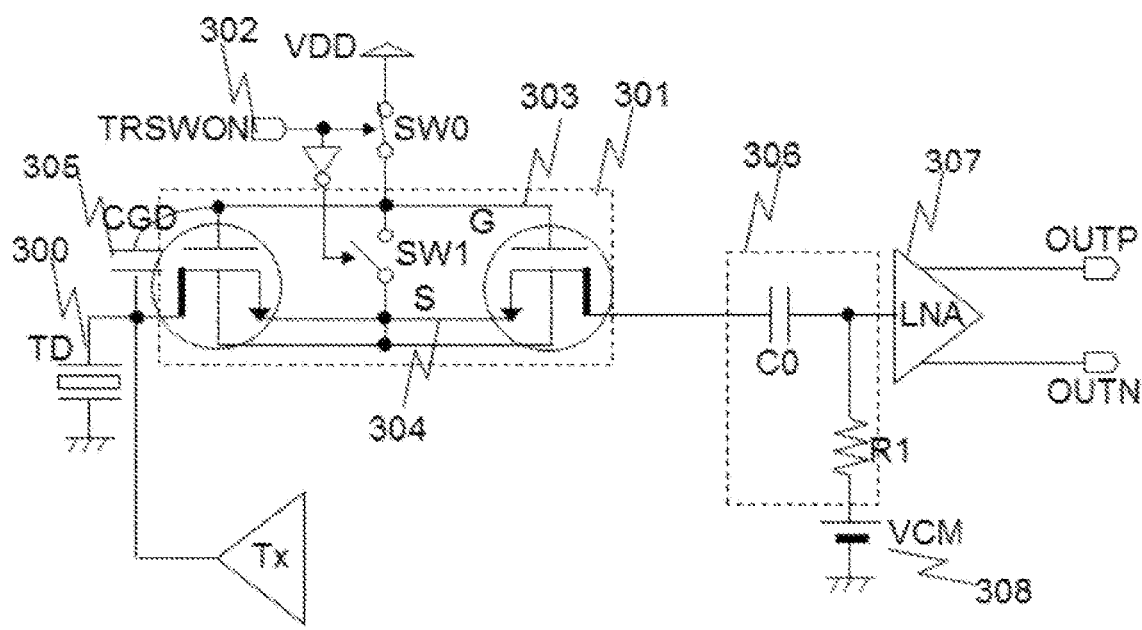
FIG. 3 is a diagram showing a circuit configuration of an ultrasonic probe of a related art.
Figure 4:
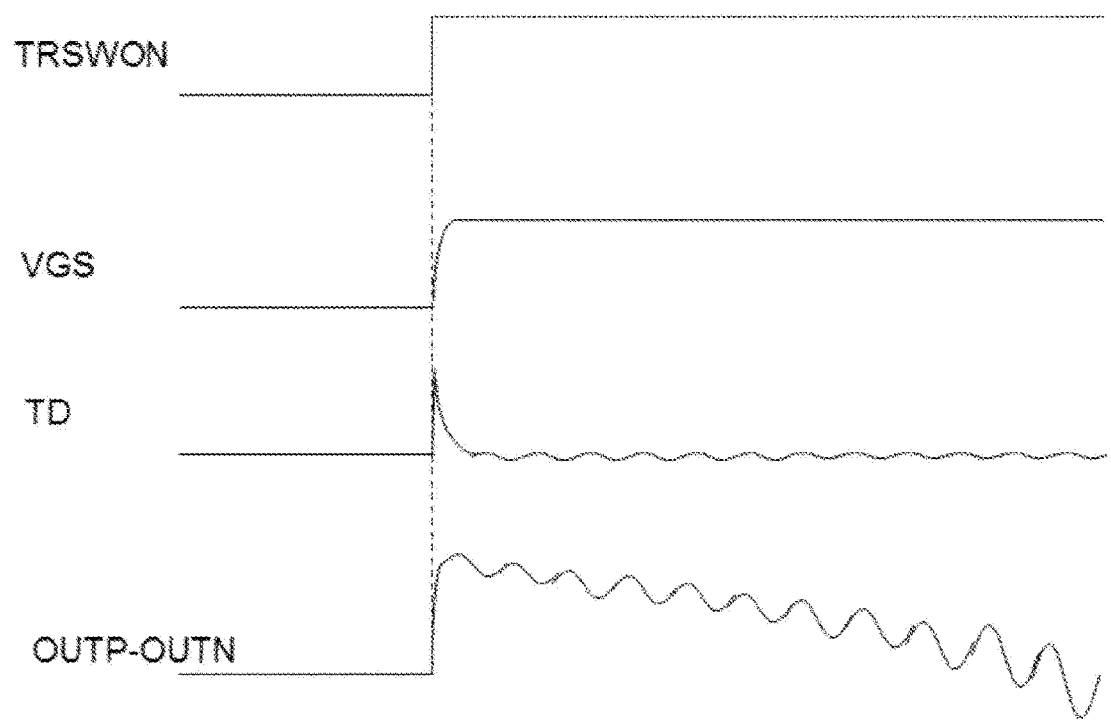
FIG. 4 is a timing chart illustrating the operation of the ultrasonic probe of the related art.

Here, in order to explain the effect of the first embodiment, a case where the present invention is not applied will be described with reference to FIGS. 3 and 4. Here, FIG. 3 shows a circuit configuration for transitioning from the transmission state to the steady reception state, and FIG. 4 shows a timing chart.

When a TRSWON 302 transitions from Lo to Hi, a TRSW 301 is turned on. However, when a voltage VGS between a gate 303 and a source 304 rapidly increases, large spike-like transmission/reception switching noise is superimposed on a transducer (TD) 300 by a parasitic capacitance 305. When spike-like transmission/reception switching noise passes through a switch circuit (TRSW) 301 and passes through a high pass filter 306 composed of the capacitor C0 and the resistor R1, a reception low noise amplifier (LNA) 307 is saturated and cannot output a desired signal.

In order to recover from saturation, the input potential of the reception low noise amplifier 307 needs to return to the vicinity of a signal common potential (VCM) 308, but the time required for this is determined by the time constant of the high pass filter 306 and the more you design to pass the low band signal, the longer it will take to recover from saturation.

As described above, in the configuration of FIG. 3 in which the first embodiment is not used, large spike-like transmission/reception switching noise is generated in a transducer 300. This transmission/reception switching noise saturates the reception circuit, so that the transmission/reception switching noise is not superimposed on the signal, but the reception impossible period continues for a long time. In the first embodiment, it is possible to prevent the reception impossible period from continuing for a long time.

As described above, the ultrasonic probe according to the first embodiment includes the transducer (100), the switch circuit (101) connected to the transducer (100), the reception circuit (103) connected to the switch circuit (101), a first switch element (SW3) connected to a reception terminal (102) provided between the switch circuit (101) and the reception circuit, a first resistance element (117: R0) connected to a control terminal (104) of the switch circuit (101), a second resistance element (R1) provided inside the reception circuit (103), and a second switch element (SW5) provided inside the reception circuit (103).

Here, the switch circuit (101) is formed of a pair of MOS transistors, and the control terminal (104) forms the gate of the MOS transistor. At least two or more elements of a first impedance (105) of the gate control terminal (104), a second impedance (106) of the reception terminal (102), a time constant (107) of the reception circuit (103), and a gain (108) of the reception circuit maintain, for a certain period of time (201) after the transmission period (200) ends, a state (state of each signal of 201) different from a steady reception state (202) which occurs after the certain period of time (201) elapses. In the different state (the state of each signal of 201) maintained for the certain period of time, a saturation signal of a constant amplitude is output.

The first impedance (105) of the gate control terminal (104) corresponds to the first resistance element (R0) connected to the gate control terminal (104). The second impedance (106) of the reception terminal (102) corresponds to the first switch element (SW3) connected to the reception terminal (102). The time constant (107) of the reception circuit (103) corresponds to the second resistance element (R1) provided inside the reception circuit (103). The gain (108) of the reception circuit corresponds to the second switch element (SW5) provided inside the reception circuit (103). In addition, at least two or more elements sequentially switch from the different states to the steady reception state, and after a certain period of time, all the elements transition to the steady reception state.

The first impedance (105) of the gate control terminal (104) is controlled by switching the resistance value of the first resistance element (R0). The gain (108) of the reception circuit (103) is controlled by switching the second switch element (SW5) provided between the differential outputs (109) of the reception circuit (103).

According to the first embodiment, it is possible to reduce a virtual image caused by transmission/reception switching noise generated upon switching from transmission to reception of ultrasonic waves. In addition, it is possible to shorten a reception impossible period due to saturation of the reception circuit by input of the transmission/reception switching noise to the reception circuit and to receive an echo from the shallow part of the body surface.

Second Embodiment

The circuit configuration of the ultrasonic probe of the second embodiment will be described with reference to FIG. 5.

As described above, the transmission/reception switching noise is caused by the coupling of a parasitic capacitance 504 of the MOSFET constituting a switch circuit (TRSW) 501. The node of a transducer (TD) 500 fluctuates by VDD×(voltage division ratio of the transducer impedance and the impedance of a CGD capacitor 504) and becomes noise when the TRSWON 505 is made to transition from Lo to Hi in FIG. 5 and a VGS of the MOS transistor (MN0) 502 and the MOS transistor (MN1) 503 rises from 0V to VDD. The noise amplitude is as follows (Math. 1).

[Math. 1]

$$V_{noise} = VDD \cdot \frac{Z_{TD}(j\omega)}{Z_{TD}(j\omega) + \frac{1}{j\omega C_{GD}}} = VDD \cdot \frac{j\omega C_{GD} \cdot Z_{TD}(j\omega)}{1 + j\omega C_{GD} \cdot Z_{TD}(j\omega)} \quad \text{(Math. 1)}$$

Where ZTD is the impedance of the transducer, j is the imaginary unit, and ω is each frequency. ZTD is a function of frequency. From this, Vnoise takes any value between 0 and VDD. There are four ways to reduce Vnoise: lower VDD, lower ZTD, lower ω, and lower CGD. When VDD is lowered, VGS of the MOS transistor becomes shallow, so that the on resistance of the switch circuit 501 is increased, thermal noise is increased, and the signal-to-noise ratio S/N of reception is degraded. If the ZTD is lowered, the load on the transmission circuit increases, and deterioration of the transmission band and the power consumption for charging/discharging of the transducer increase. Lowering ω, ie, lowering the frequency, means increasing VGS slowly. This is to turn on the switch circuit 501 slowly by limiting the gate charging current by the resistor R0 as shown in FIGS. 1 and 2.

Figure 5:
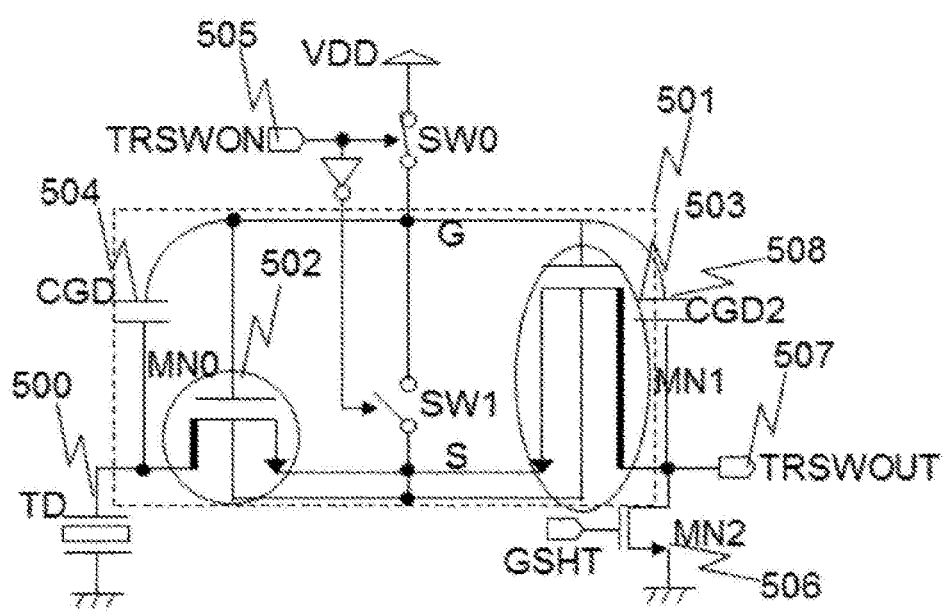
FIG. 5 is a diagram showing a circuit configuration of an ultrasonic probe of a second embodiment.

The method of lowering the CGD 504 in the last order can be realized by reducing a channel width Wg of the MN0 502 in FIG. 5. However, if the channel width Wg is reduced, the on resistance also increases. Therefore, the channel width Wg of the MN0 502 is made smaller than the channel width Wg of the MN1 503. The on resistance as the switch circuit 501 is a series resistance of the on resistance of the MN0 502 and the on resistance of the MN1 503. Here, even if the channel width Wg of the MN0 502 is changed to 0.5 times and the channel width Wg of the MN1 503 is changed to 1.5 times from the state where the channel widths Wg of the MN0 502 and the MN1 503 are the same size, the area and the on resistance of the switch circuit 501 do not change.

However, since the parasitic capacitance CGD 504 of the MOS transistor depends on the channel width Wg, the CGD 504 of the MN0 502 is 0.5 times the original. The CGD2 (508) of the MN1 503 is 1.5 times larger, but if the low-voltage NMOS switch MN2 (506) is turned on, a TRSWOUT 507 is fixed to GND, and the fluctuation of the TRSWOUT 507 due to CGD2 (508) coupling of the MN1 503 is very small. From this, the value of the MN0 502 on the transducer 500 side is decreased and the size of the MN1 503 on the reception side is increased, and the size is unbalanced, thereby reducing transmission/reception switching noise while keeping the area and the on resistance of the switch circuit 501 constant. The difference between the size of the MN0 502 and the size of the MN1 503 in FIG. 5 represents the difference of the channel width Wg.

Generally, the minimum channel width Wg of the MOS transistor (MOSFET) is limited by the size of the source-drain contact and the lithography accuracy by the semiconductor process, and the channel width Wg ratio of MN0 502 and MN1 503 is not arbitrarily determined but is restricted by the semiconductor process.

As described above, in the ultrasonic probe according to the second embodiment, among the pair of MOS transistors (502, 503) forming the switch circuit (501), the first channel width of the first MOS transistor (502) positioned on the transducer (500) side is configured to be smaller than the second channel width of the second MOS transistor (503) positioned on the reception terminal (102) side.

According to the second embodiment, it is possible to reduce the virtual image caused by the transmission/reception switching noise generated upon switching from transmission to reception of ultrasonic waves.

Third Embodiment

Figure 6:
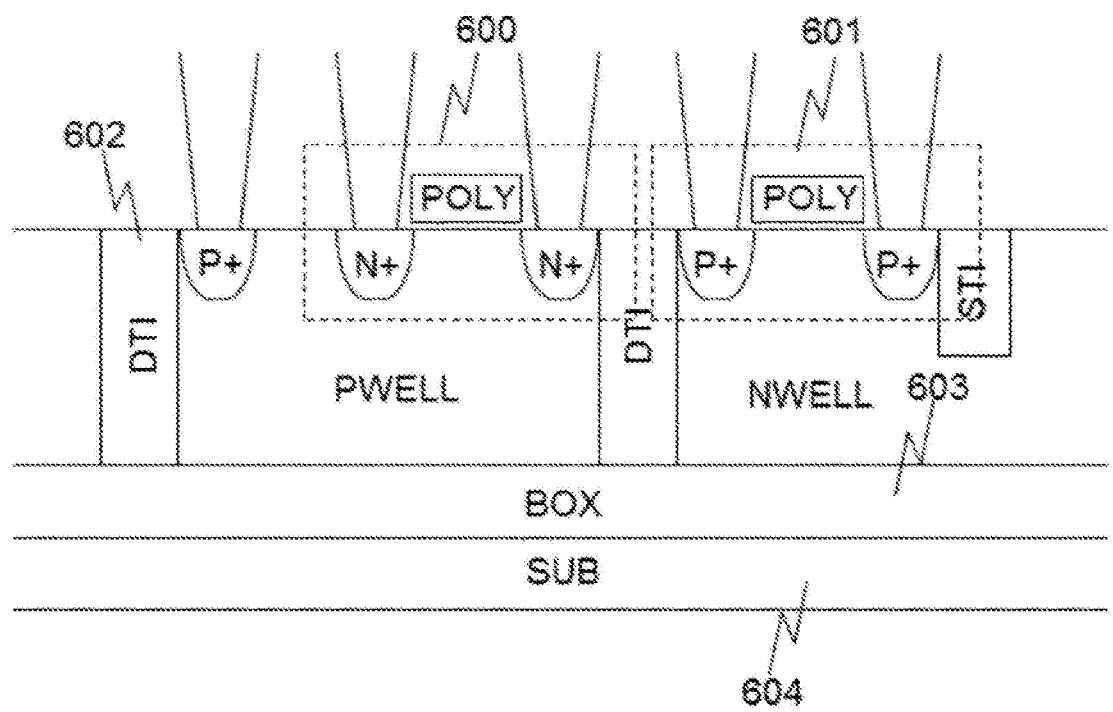
FIG. 6 is a diagram showing a circuit configuration of an ultrasonic probe of a third embodiment.

The circuit configuration of the ultrasonic probe of the third embodiment will be described with reference to FIG. 6. FIG. 6 shows a case of realizing the SW3 in FIG. 1 by an NMOS switch, that is, a layout example of the circuit configuration of the MN2 (506) in FIG. 5, as a device cross-sectional view.

As described above, the potential of the transducer is 0V common, and positive and negative voltages pass through the switch circuit (TRSW). If a strong echo is received, the NMOS parasitic body diode connected to the TRSW output to GND becomes the forward direction by a deep negative voltage, which may trigger latch-up and destroy the IC.

In order to prevent this, it is necessary to isolate the NMOS element 600 alone so that the MN2 does not form a parasitic thyristor with another PMOS element 601. For this purpose, an SOI (Silicon On Insulator) wafer may be used in which a buried oxide (BOX) 603 is embedded.

The NMOS element 600 composed of N+ source/drain and a gate of POLY silicon can prevent latch-up by being laid out in a state electrically isolated from another element not by shallow element isolation (STI (Shallow Trench Isolation)) but by DTI (Deep Trench Isolation) 602 reaching a BOX.

As described above, in the ultrasonic probe of the third embodiment, the first switch element (SW3) is composed of an NMOS element (600) connected between the reception terminal (102) of the switch circuit (101) and the ground terminal. The second impedance (106) of the reception terminal (102) is controlled by the NMOS element (600). The NMOS element (600) is composed of an FET formed on an SOI substrate (604). The NMOS element (600) is electrically isolated by being surrounded by the DTI (602).

According to the third embodiment, it is possible to reduce the virtual image caused by the transmission/reception switching noise generated upon switching from transmission to reception of ultrasonic waves.

Fourth Embodiment

The ultrasonic transmission/reception switching method of the fourth embodiment will be described with reference to FIG. 7.

Figure 7:
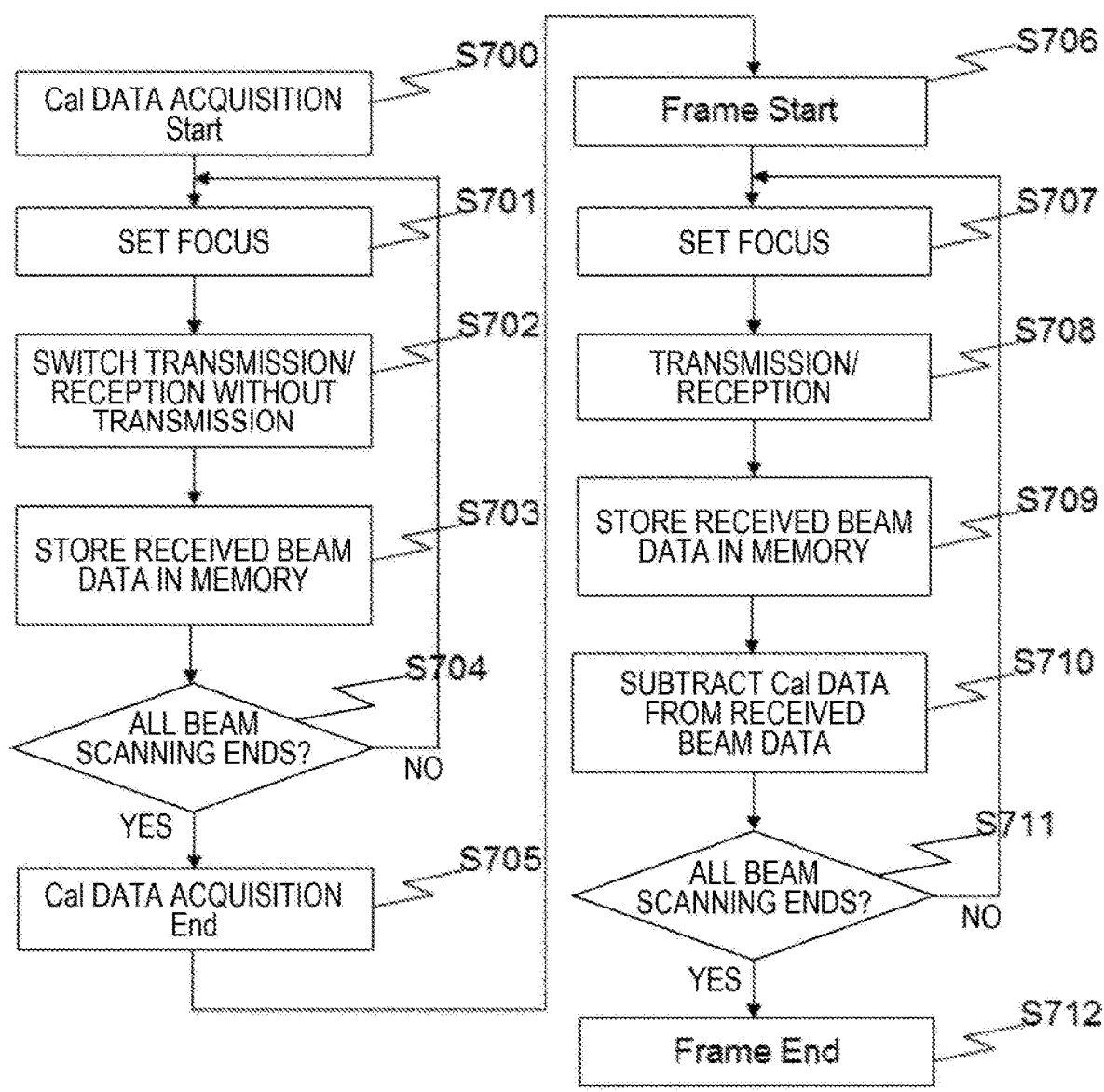
FIG. 7 is a flowchart illustrating an ultrasonic transmission/reception switching method of a fourth embodiment.

FIG. 7 shows an image acquisition method for reducing the influence of transmission/reception switching noise on an image as a whole system of an ultrasonic diagnostic apparatus.

Assuming that reception saturation due to transmission/reception switching noise is prevented, in order to prevent switching noise from being displayed as a virtual image in the image, transmission/reception switching noise data is acquired in advance for calibration, and this may be subtracted from actual image data.

As shown in FIG. 7, first, Cal data for calibration is acquired (S700).

Next, a delay corresponding to the scanning angle and focus is set (S701), transmission/reception is switched without transmission (S702), and received beam data of the scanning line is acquired (S703). Although not particularly limited, the scanning line data digitized by the A/D converter is stored in the memory in the main unit.

Next, Cal data of all the scanning lines are acquired by changing the scanning angle (S704), and the Cal data acquisition ends (S705). Although not particularly limited, since this Cal data acquisition wants to acquire only transmission/reception switching noise, it is preferable to leave the probe in the air so as not to return an echo due to reflection.

If Cal data is acquired once before product shipment and stored in the non-volatile memory, transmission/reception switching noise is always the same except for aging of the device in the IC. Therefore, it is not necessary to acquire Cal data every time of image acquisition.

Next, normal transmission and reception are performed to acquire a 2D image frame or 3D image volume (S706). Next, a delay corresponding to the scanning angle and focus is set (S707), transmission/reception is performed (S708), and received beam data of the scanning line is acquired and stored in memory (S709). Next, the Cal data is subtracted from the received beam data (S710) and a determination is made of whether all beam scanning ends (S711). If it is determined that the the beam scanning is not complete, the focus is set again (S707), and if it is determined that the beam scanning ends, the image acquisition ends (S712).

If Cal data is subtracted from the received beam data of the scanning line (S710), received beam data from which transmission/reception switching noise is subtracted is acquired, and an image with a reduced virtual image is acquired. The subtraction of the Cal data from the received beam data may be performed each time received beam data is acquired as shown in FIG. 7 or may be performed collectively after whole beam data is acquired.

Fifth Embodiment

The circuit configuration of the ultrasonic probe of the fifth embodiment will be described with reference to FIG. 8.

Figure 1:
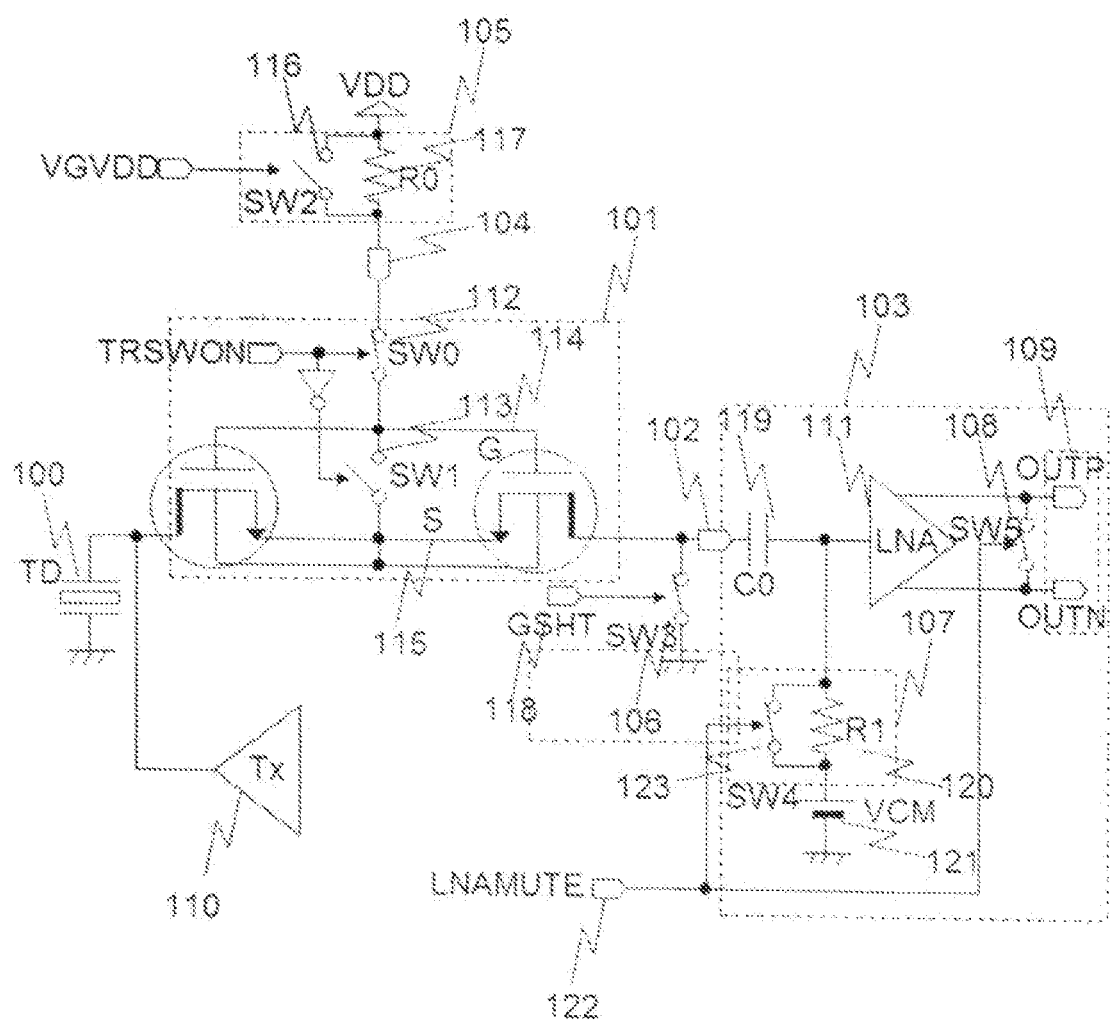
FIG. 1 is a diagram showing a circuit configuration of an ultrasonic probe of a first embodiment.

In FIG. 1, since the reception low noise amplifier 111 is a single-ended input and a differential output, the output can be stopped by inserting the switch (SW5) between the differential outputs.

Figure 8:
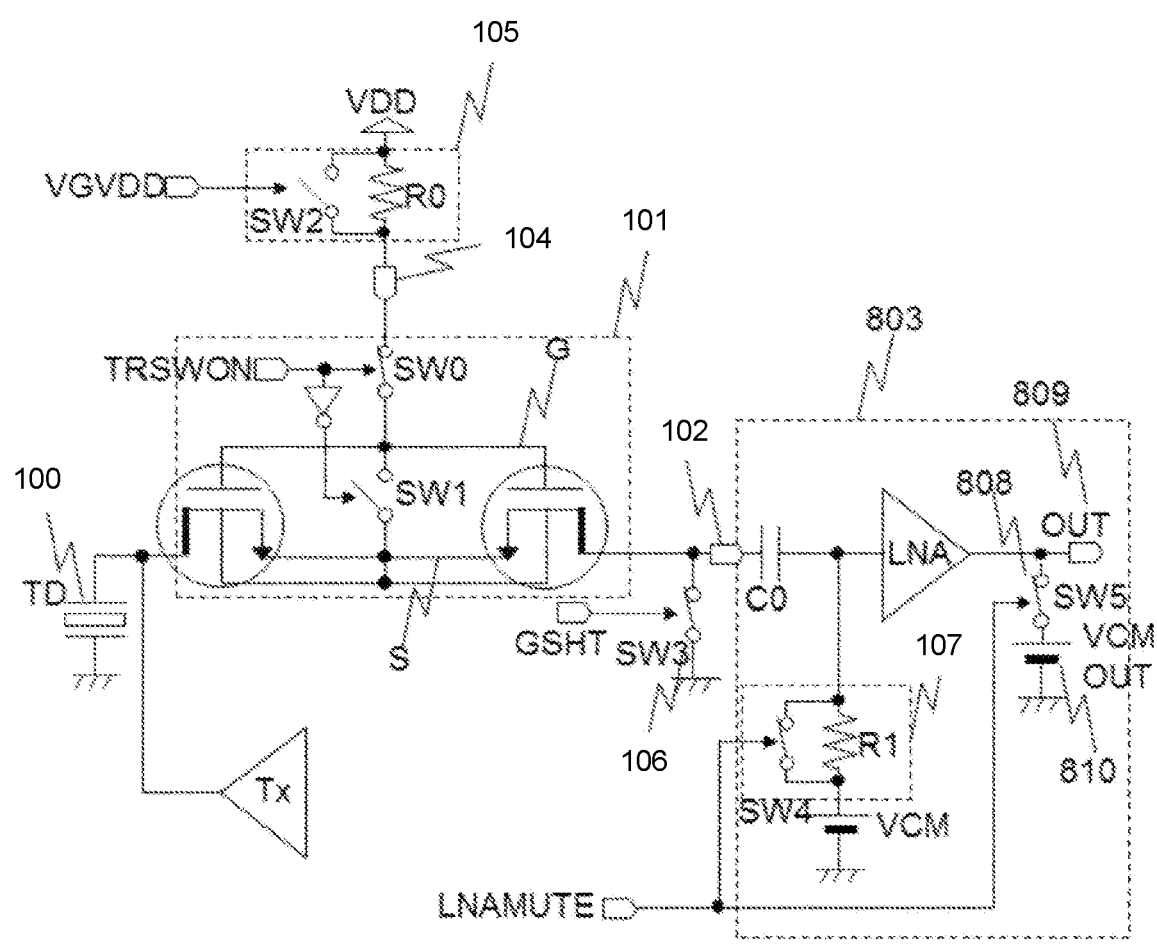
FIG. 8 is a diagram showing a circuit configuration of an ultrasonic probe of a fifth embodiment.

When the reception low noise amplifier (LNA) has a single-ended output 809, the output common voltage VCMOUT 810 of the reception low noise amplifier (LNA) is prepared in advance as shown in FIG. 8, and the output 809 of the reception low noise amplifier (LNA) may be shorted to the VCMOUT 810 by the switch SW5 (808) during a period in which it is desired to stop the output.

Although the second harmonic distortion of the signal can be reduced by making the reception low noise amplifier (LNA) have a differential output, power consumption generally increases in a case of a differential circuit configuration. In the fifth embodiment, although the second harmonic distortion is degraded, power consumption can be reduced by using a single-ended output. The other configuration is the same as the circuit configuration of the ultrasonic probe of the first embodiment shown in FIG. 1, and thus the description thereof is omitted.

As described above, in the ultrasonic probe of the fifth embodiment, the gain of the reception circuit (803) is controlled by short-circuiting the single end output (809) of the reception circuit (803) by the second switch element (808: SW5) connected to the DC output common voltage (810).

According to the fifth embodiment, it is possible to reduce the virtual image caused by the transmission/reception switching noise generated upon switching from transmission to reception of ultrasonic waves.

Sixth Embodiment

The configuration of the ultrasonic diagnostic apparatus of the sixth embodiment will be described with reference to FIGS. 9 and 10.

Figure 9:
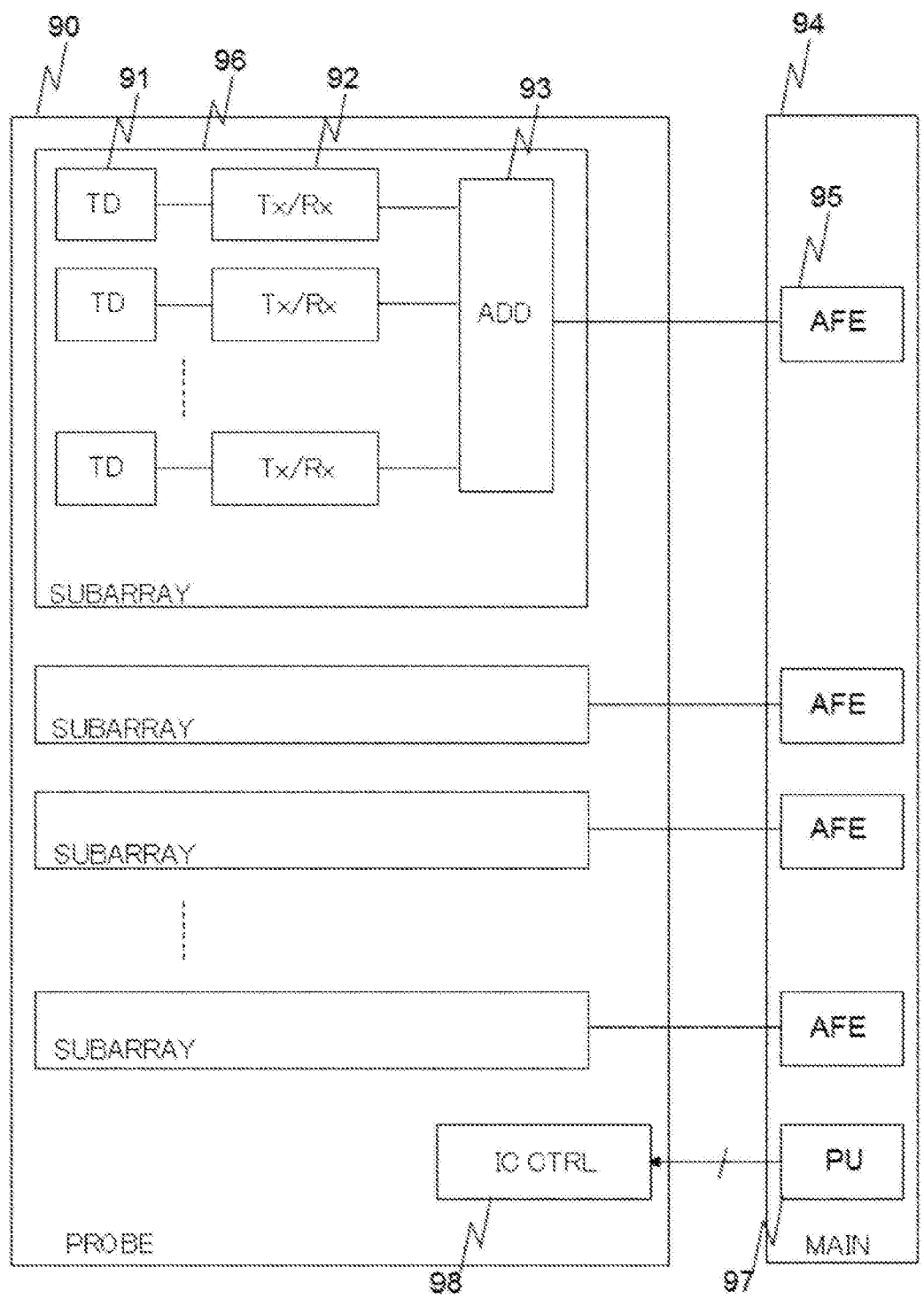
FIG. 9 is a diagram showing the configuration of an ultrasonic diagnostic apparatus of a sixth embodiment.

FIG. 9 shows an ultrasonic probe having a two-dimensional array transducer for three-dimensional imaging and a system configuration.

The ultrasonic diagnostic apparatus of the sixth embodiment has an ultrasonic probe 90 and a main unit (MAIN) 94. In the ultrasonic probe 90, a transmission/reception circuit (Tx/Rx) 92 is disposed for each transducer (TD) 91, and the received signals are added by an adder circuit 93 and sent to an AFE (analog front end) 95 in the main unit 94. A grouping unit of transducer channels to be added is called a subarray 96.

The processor (PU) 97 in the main unit 94 sends a control signal to an IC control logic circuit (IC CTRL) 98 in the ultrasonic probe 90, and the IC control logic circuit 98, in response to this, performs switching between transmission and reception and delay control for ultrasonic focusing. Although not particularly limited, when the transmission circuit is a pulser system instead of a linear amplifier system, the waveform is sent to the pulser as a digital value, so the IC control logic circuit 98 includes a waveform memory for storing waveform data transmitted by the pulser.

Figure 10:
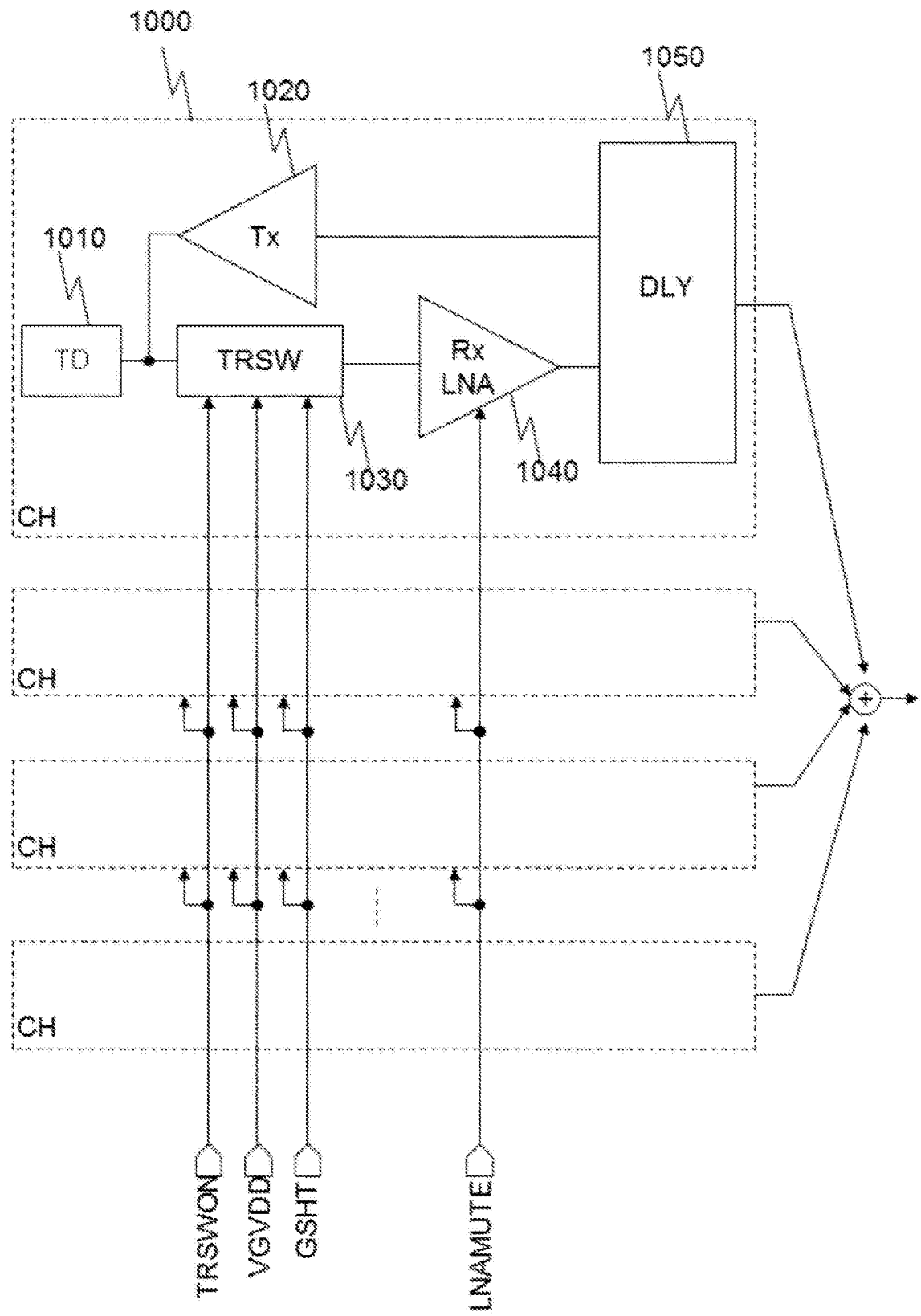
FIG. 10 is a diagram showing a configuration example of a sub array of an IC in an ultrasonic probe.

The configuration within the subarray is shown in FIG. 10.

A transmission/reception circuit 1000 per transducer includes a transmission circuit (Tx) 1020 that is composed of a high voltage MOS transistor, generates a high voltage signal, and drives a transducer (TD) 1010, a transmission/reception separation switch (TRSW) 1030 that is turned off at the time of transmission, protects the low-voltage reception circuit from the high voltage signal, and passes a minute signal at the time of reception, a low-voltage reception low noise amplifier (LNA) 1040, and a micro delay circuit (DLY) 1050 that performs phase alignment by delaying the transmission signal, performing beam-forming, and further delaying the received signal. The received signals phased by the minute delay circuit are added and sent to the main unit 94.

A control signal group is generated by, but not particularly limited to, a logic circuit and distributed to each transmission/reception circuit 1000. In order to reduce the number of wiring lines, only TRSWON may be wired, and logic circuits may be provided in each transmission/reception circuit 1000 to generate VGVDD, GSHT, and LNAMUTE control signals from the TRSWON signal.

As described above, the ultrasonic diagnostic apparatus of the sixth embodiment includes the ultrasonic probe (90) and the main unit (94). The ultrasonic probe (90) includes a plurality of transducers (91), a plurality of transmission/reception circuits (92) respectively provided corresponding to the plurality of transducers (91) and switching ultrasonic waves from transmission to reception, an adder circuit (93) for adding the outputs of the plurality of transmission/reception circuits (92), and a control circuit (98) for controlling transmission/reception switching. The main unit (94) receives the output of the adder circuit (93) and transmits a predetermined control signal to the control circuit (98).

As shown in FIG. 1, the ultrasonic probe (90) includes a switch circuit (101) connected to the transducer (100), a reception circuit (103) connected to the switch circuit (101), a first switch element (SW3) connected to a reception terminal (102) provided between the switch circuit (101) and the reception circuit, a first resistance element (R0) connected to the control terminal (104) of the switch circuit (101), a second resistance element (R1) provided inside the reception circuit (103), and a second switch element (SW5) provided inside the reception circuit (103).

As shown in FIGS. 1 and 2, the switch circuit (101) is composed of a pair of MOS transistors, and the control terminal (104) forms a gate control terminal of the MOS transistor. The control circuit (98) controls so that at least two or more elements of a first impedance (105) of the gate control terminal (104), a second impedance (106) of the reception terminal (102), a time constant (107) of the reception circuit (103), and a gain (108) of the reception circuit maintain, for a certain period of time (201) after the transmission period (200) ends, a state (state of each signal of 201) different from a steady reception state (202) which occurs after the certain period of time (201) elapses. Further, the control circuit (98) controls so that a saturation signal of a constant amplitude is output in different states (states of respective signals of 201) maintained for a certain period of time.

According to the above-described embodiment, it is possible to reduce a virtual image caused by transmission/reception switching noise generated upon switching from transmission to reception of ultrasonic waves. In addition, it is possible to shorten a reception impossible period due to saturation of the reception circuit by input of the transmission/reception switching noise to the reception circuit and to receive an echo from the shallow part of the body surface.

As described above, according to the above-described embodiment, it is possible to realize an ultrasonic diagnostic apparatus capable of performing highly reliable ultrasonic imaging with a small virtual image and targeting up to the shallow part of the body surface.

What is claimed is:

1. An ultrasonic probe comprising:
a transducer;
a switch circuit connected to the transducer; a reception circuit connected to the switch circuit;
a first switch element connected to a reception terminal provided between the switch circuit and the reception circuit;
a first resistance element disposed outside of the switch circuit and connected to a control terminal of the switch circuit;
a second resistance element provided inside the reception circuit;
a second switch element provided inside the reception circuit;
a third switch element provided inside the reception circuit; and
a capacitor provided inside the reception circuit; wherein
the switch circuit is composed of a pair of MOS transistors;
the control terminal constitutes a gate of each of the pair of MOS transistors;
at least two or more elements of a first impedance of the control terminal, a second impedance of the reception terminal, a time constant of the reception circuit, and a gain of the reception circuit sequentially switch, in a certain period of time after a transmission period ends, from a different state to a steady reception state, the different state being different from the steady reception state which occurs after the certain period of time elapses;
the first impedance of the control terminal is determined by the first resistance element connected to the control terminal;
the second impedance of the reception terminal is determined by the first switch element connected to the reception terminal;
in the certain period of time, the time constant of the reception circuit is a first time constant which is determined by the capacitor and a resistance of the third switch element;
in a steady reception period after the certain period of time, the time constant of the reception circuit is a second time constant which is determined by the capacitor and the second resistance element provided inside the reception circuit, the first time constant is smaller than the second time constant; and
the gain of the reception circuit is determined by the second switch element provided inside the reception circuit.

2. The ultrasonic probe according to claim 1, wherein a saturation signal is not output in the different state maintained for the certain period of time.

3. The ultrasonic probe according to claim 1, wherein the first impedance of the control terminal is controlled by switching a resistance value of the first resistance element.

4. The ultrasonic probe according to claim 1, wherein the gain of the reception circuit is controlled by switching the second switch element provided between differential outputs of the reception circuit.

5. The ultrasonic probe according to claim 1, wherein the gain of the reception circuit is controlled by short-circuiting a single-ended output of the reception circuit by the second switch element connected to a DC output common voltage.

6. The ultrasonic probe according to claim 1, wherein
the first switch element is composed of a transistor connected between the reception terminal of the switch circuit and a ground terminal, and
the second impedance of the reception terminal is controlled by the transistor.

7. The ultrasonic probe according to claim 6, wherein
the transistor is composed of an FET formed on an SOI substrate, and
the FET is electrically isolated by being surrounded by DTI.

8. The ultrasonic probe according to claim 2, wherein among the pair of MOS transistors constituting the switch circuit, a first channel width of the first MOS transistor positioned on the transducer side is configured to be smaller than a second channel width of the second MOS transistor positioned on the reception terminal side.

9. The ultrasonic probe according to claim 1, wherein the first resistance element is directly connected to the control terminal of the switch circuit without any circuit elements therebetween.

10. An ultrasonic diagnostic apparatus comprising:
an ultrasonic probe including
a plurality of transducers,
a transmission/reception circuit that is provided corresponding to each of the plurality of transducers and switches an ultrasonic wave from transmission to reception,
an adder circuit that adds outputs of a plurality of the transmission/reception circuits, and
a control circuit that controls the transmission to the reception switching; and
a main unit that receives an output of the adder circuit and transmits a predetermined control signal to the control circuit,
the ultrasonic probe having
a switch circuit connected to the plurality of transducers,
a reception circuit connected to the switch circuit,
a first switch element connected to a reception terminal provided between the switch circuit and the reception circuit,
a first resistance element disposed outside of the switch circuit and connected to a control terminal of the switch circuit,
a second resistance element provided inside the reception circuit,
a second switch element provided inside the reception circuit,
a third switch element provided inside the reception circuit, and
a capacitor provided inside the reception circuit, wherein
the switch circuit is composed of a pair of MOS transistors;
the control terminal constitutes a gate of each of the pair of MOS transistors;
at least two or more elements of a first impedance of the control terminal, a second impedance of the reception terminal, a time constant of the reception circuit, and a gain of the reception circuit sequentially switch, in a certain period of time after a transmission period ends, from a different state to a steady reception state, the different state being different from the steady reception state which occurs after the certain period of time elapses;
the first impedance of the control terminal is determined by the first resistance element connected to the control terminal;

the second impedance of the reception terminal is determined by the first switch element connected to the reception terminal;

in the certain period of time, the time constant of the reception circuit is a first time constant which is determined by the capacitor and a resistance of the third switch element;

in a steady reception period after the certain period of time, the time constant of the reception circuit is a second time constant which is determined by the capacitor and the second resistance element provided inside the reception circuit, the first time constant is smaller than the second time constant; and the gain of the reception circuit is determined by the second switch element provided inside the reception circuit.

11. The ultrasonic diagnostic apparatus according to claim 10, wherein the control circuit controls so that a saturation signal is not output in the different state maintained for the certain period of time.

12. The ultrasonic diagnostic apparatus according to claim 10, wherein the first resistance element is directly connected to the control terminal of the switch circuit without any circuit elements therebetween.

* * * * *